(12) United States Patent
Richmann et al.

(10) Patent No.: US 10,022,260 B2
(45) Date of Patent: Jul. 17, 2018

(54) OSTOMY POUCH

(71) Applicant: Hollister Incorporated, Libertyville, IL (US)

(72) Inventors: Sussie Richmann, Hellebaek (DK); Christen Grum-Schwensen, Hillerød (DK); Claus Rasmussen, Værløse (DK); Peter Møller-Jensen, Hornbæk (DK); Tue Kjaergaard Toft, Copenhagen S (DK); Jan Clausen, Værløse (DK); Iben Frellesvig, Copenhagen Ø (DK); Michael Stenvang, Skodsborg (DK)

(73) Assignee: HOLLISTER INCORPORATED, Libertyville, IL (US)

( * ) Notice: Subject to any disclaimer, the term of this patent is extended or adjusted under 35 U.S.C. 154(b) by 317 days.

(21) Appl. No.: 14/402,019

(22) PCT Filed: May 31, 2013

(86) PCT No.: PCT/US2013/043534
§ 371 (c)(1),
(2) Date: Nov. 18, 2014

(87) PCT Pub. No.: WO2013/181493
PCT Pub. Date: Dec. 5, 2013

(65) Prior Publication Data
US 2015/0209172 A1 Jul. 30, 2015

(30) Foreign Application Priority Data
May 31, 2012 (EP) .................................... 12170216

(51) Int. Cl.
*A61F 5/44* (2006.01)
*A61F 5/445* (2006.01)

(52) U.S. Cl.
CPC ............ *A61F 5/4404* (2013.01); *A61F 5/445* (2013.01); *A61F 5/4407* (2013.01)

(58) Field of Classification Search
CPC combination set(s) only.
See application file for complete search history.

(56) References Cited

U.S. PATENT DOCUMENTS

| 3,055,368 A * | 9/1962 | Baxter ................... A61F 5/441 |
| | | 128/DIG. 24 |
| 3,570,490 A | 3/1971 | Berger |
| (Continued) | | |

FOREIGN PATENT DOCUMENTS

| EP | 2637613 B1 | 10/2015 |
| JP | 2007536042 A | 12/2007 |
| (Continued) | | |

OTHER PUBLICATIONS

International Preliminary Report on Patentability for PCT/US2013/043534.

*Primary Examiner* — Philip R Wiest
*Assistant Examiner* — Guy K Townsend
(74) *Attorney, Agent, or Firm* — Levenfield Pearlstein, LLC

(57) ABSTRACT

The present disclosure concerns an ostomy pouch comprising a first pouch wall and a second pouch wall joined together along a peripheral seal to form a cavity for accommodating waste material; and said pouch having an upper and a lower portion; an inlet provided in the first pouch wall for receiving waste into the pouch; said inlet opening being provided in the upper portion; wherein the pouch further comprises a top view member comprising two layers of transparent flexible film is provided an upper section of said upper portion between said first and second pouch walls and sealed to either the first or the second wall by peripheral (Continued)

seals, wherein said top view member is provided with a lowermost edge.

10 Claims, 2 Drawing Sheets

(56) References Cited

U.S. PATENT DOCUMENTS

| | | | | |
|---|---|---|---|---|
| 4,084,590 A * | 4/1978 | Caraway | ............... | A61F 5/445 604/335 |
| 4,300,560 A * | 11/1981 | Steer | ............... | A61F 5/445 604/335 |
| 4,367,742 A * | 1/1983 | Ornstein | ............... | A61F 5/441 128/DIG. 24 |
| 4,372,308 A * | 2/1983 | Steer | ............... | A61F 5/441 604/333 |
| 4,403,991 A * | 9/1983 | Hill | ............... | A61F 5/443 604/337 |
| 4,465,486 A * | 8/1984 | Hill | ............... | A61F 5/443 24/30.5 R |
| 4,519,797 A * | 5/1985 | Hall | ............... | A61F 5/445 604/332 |
| 4,755,177 A * | 7/1988 | Hill | ............... | A61F 5/443 604/336 |
| 4,911,699 A * | 3/1990 | Fenton | ............... | A61F 5/441 604/333 |
| 5,354,132 A | 10/1994 | Young | | |
| 5,591,144 A * | 1/1997 | Smith | ............... | A61F 5/445 604/327 |
| 5,667,502 A | 9/1997 | Holtermann | | |
| 5,759,180 A * | 6/1998 | Myhres | ............... | A61F 5/445 428/343 |
| 5,865,819 A * | 2/1999 | Cisko, Jr. | ............... | A61F 5/445 604/327 |
| 5,938,647 A * | 8/1999 | Smith | ............... | A61F 5/445 128/DIG. 24 |
| 6,135,986 A * | 10/2000 | Leisner | ............... | A61F 5/441 604/322 |
| 6,620,474 B1 * | 9/2003 | Regnier | ............... | B32B 27/28 428/35.7 |
| 6,884,480 B2 * | 4/2005 | Bradfute | ............... | B32B 27/30 428/34.9 |
| 2004/0059306 A1 * | 3/2004 | Tsal | ............... | A61F 5/4404 604/332 |
| 2004/0143230 A1 * | 7/2004 | Hansen | ............... | A61F 5/4404 604/333 |
| 2005/0075616 A1 * | 4/2005 | Holter | ............... | A61F 5/445 604/332 |
| 2005/0107758 A1 * | 5/2005 | Hogan | ............... | A61F 5/445 604/327 |
| 2005/0113770 A1 * | 5/2005 | Pedersen | ............... | A61F 5/448 604/332 |
| 2005/0143696 A1 * | 6/2005 | Pedersen | ............... | A61F 5/441 604/332 |
| 2005/0177119 A1 * | 8/2005 | Tsai | ............... | A61F 5/445 604/332 |
| 2005/0261645 A1 * | 11/2005 | Conrad | ............... | A61F 5/445 604/332 |
| 2007/0005033 A1 * | 1/2007 | Ciok | ............... | A61F 5/443 604/344 |
| 2007/0255240 A1 * | 11/2007 | Ciok | ............... | A61F 5/445 604/339 |
| 2007/0270772 A1 | 11/2007 | Worosee | | |
| 2007/0279772 A1 * | 12/2007 | Hsueh | ............... | G02B 7/102 359/826 |
| 2008/0065031 A1 * | 3/2008 | Turner | ............... | A61F 5/4407 604/332 |
| 2008/0154220 A1 * | 6/2008 | Gaffney | ............... | A61F 5/445 604/333 |
| 2008/0226864 A1 * | 9/2008 | Willis | ............... | A61F 5/4405 428/98 |
| 2008/0294129 A1 * | 11/2008 | Giori | ............... | A61F 5/445 604/332 |
| 2008/0306459 A1 * | 12/2008 | Albrectsen | ............... | A61F 5/441 604/333 |
| 2011/0190718 A1 | 8/2011 | Wheaton et al. | | |
| 2011/0238024 A1 * | 9/2011 | Smith | ............... | A61F 5/445 604/336 |
| 2013/0072886 A1 * | 3/2013 | Schertiger | ............... | A61F 5/441 604/333 |
| 2015/0209172 A1 * | 7/2015 | Richmann | ............... | A61F 5/4404 604/332 |

FOREIGN PATENT DOCUMENTS

| | | |
|---|---|---|
| JP | 2013526989 A | 6/2013 |
| WO | 2008150991 A2 | 12/2008 |
| WO | 2011150936 A1 | 12/2011 |

* cited by examiner

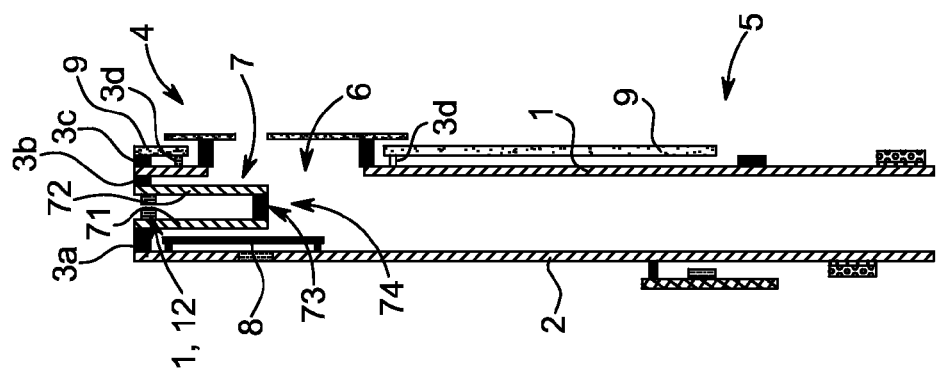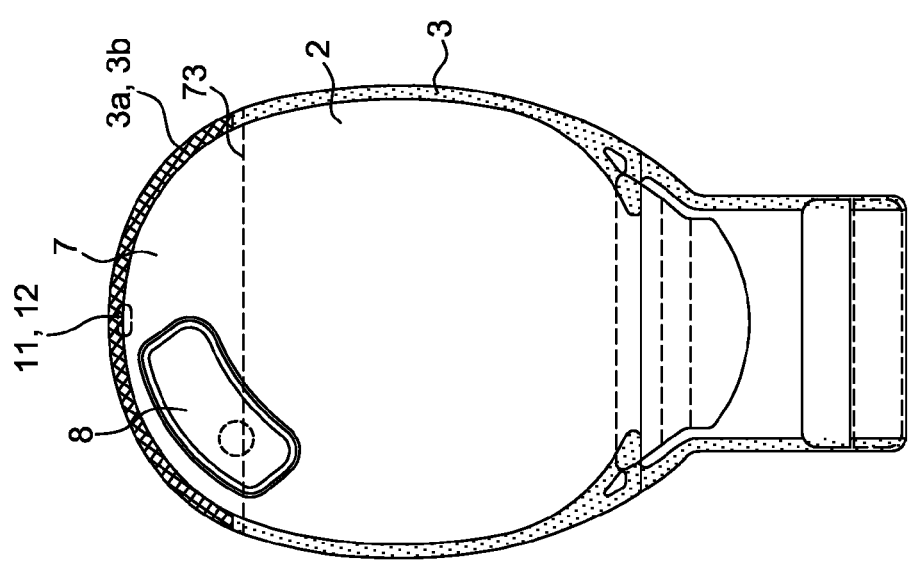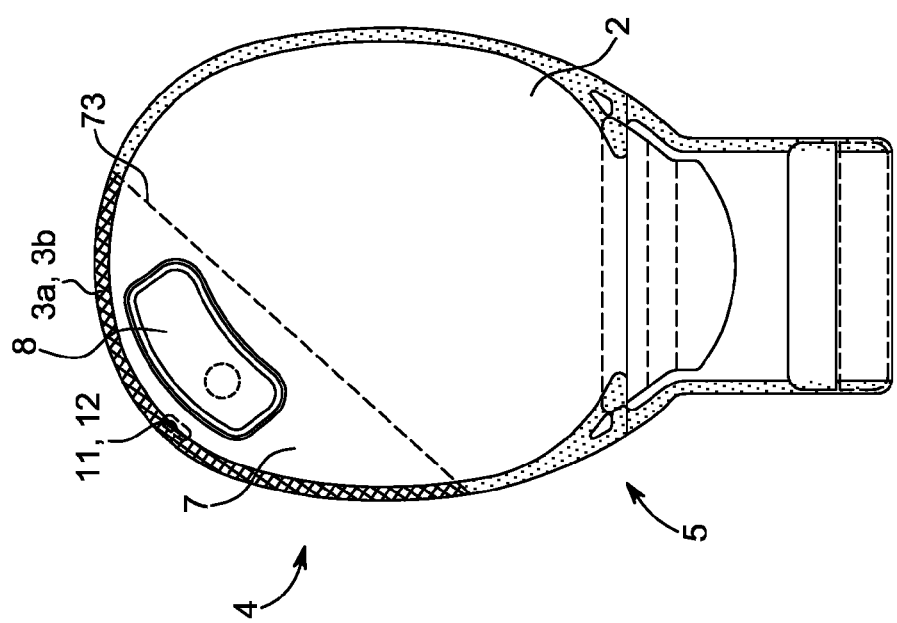

OSTOMY POUCH

CROSS-REFERENCE TO RELATED APPLICATIONS

This is a National Stage Application of International Patent Application No. PCT/US2013/043534, filed May 31, 2013, which claims the benefit of and priority to European Application No. 12170216.1, filed May 31, 2012, the contents of which are incorporated fully by reference herein.

FIELD OF THE DISCLOSURE

The present disclosure relates to an ostomy pouch comprising a first pouch wall and a second pouch wall joined together along a peripheral seal to form a cavity for accommodating waste material; and the pouch having an upper and a lower portion, an inlet provided in the first pouch wall for receiving waste into the pouch, wherein the inlet opening is provided in the upper portion.

BACKGROUND

When applying an ostomy pouch, it is important that the pouch is correctly positioned around the stoma. In order to ensure proper positioning it is desirable for the user to inspect the stoma. As the stoma will be covered by the pouch, this inspection can take place by looking through an ostomy pouch with transparent side walls or at least a transparent portion of the side walls. Examples of such pouches are known from e.g. U.S. Pat. No. 3,570,490 and WO 2008/150991.

In the pouch disclosed in WO 2008/150991 two panels are provided, one panel covering on the top of the pouch and a second panel covering the lower part of the pouch. These two panels are slightly overlapping without being sealed to each other across the pouch. This arrangement allows the user to manually separate the overlap to inspect the condition of the stoma.

Although this allows for visual inspection of the stoma, during the application of the pouch onto the user's skin it can be difficult for the user to see what he or she is doing since the user will be looking at the stoma area from the top. It is most likely that the user will position the pouch and inspect the stoma condition via a mirror. This however may be somewhat inconvenient and difficult as this only gives the user an indirect view of the stoma and the pouch. In some situations the user may be assisted where it may be a nurse or other healthcare staff who will inspect and change the ostomy pouch. In this situation the assistant will have a better direct view, but he or she is not always available for the ostomy pouch user. So although visible inspection is possible it is inconvenient for the user to do.

SUMMARY

It is an object of the present disclosure to provide an ostomy pouch which is easier to apply and allows for easier inspection of the stoma.

This object is achieved by providing an ostomy pouch of the initially mentioned kind wherein the pouch further comprises a top view member comprising two layers of film, wherein at least one is a transparent flexible film, and wherein said two films are provided on an upper section of said upper portion between said first and second pouch walls and sealed to either the first or the second wall by peripheral seals, wherein said top view member is provided with a lowermost edge.

The provision of a top view member is advantageous as this allows for viewing the inside of the pouch. This makes it easier for the wearer to position an ostomy pouch, i.e. a one piece ostomy pouch, around the stoma whilst at the same time still provides the discretion that a beige or otherwise opaque pouch provides. Furthermore, the pouch according to the disclosure is advantageous as it allows the user to view the peristomal area of the barrier, so that leakage, skin irritation, barrier erosion or the like can be detected at an early stage and earlier than usual on beige pouches. In addition, if the pouch is provided with a flatus gas filter the top view member can act as a filter protection by avoiding matter from the stoma in reaching and clogging the filter.

Moreover, the solution of having a top view member for visual inspection may also be found advantageous as it allows for having two beige films forming the pouch. This results in a beige pouch which allows for a more discretional use of the pouch when worn by the user.

In a first embodiment, the top view member comprises first and second sheet layers which are sealed together along their lower edges to provide the lowermost edge of the top view member, the first sheet layer is sealed to the first side wall along their common peripheral edge, and the second sheet layer is sealed to the second side wall along their common peripheral edge.

In a second embodiment, the top view member comprises a single transparent sheet which is folded to form the lowermost edge and two sheet layers which are sealed to the first side wall and the second side wall, respectively.

In one embodiment, the lowermost edge of the top view member is provided with a horizontal orientation, i.e. perpendicular to the longitudinal direction of the pouch. This may be relatively simple to manufacture. As an alternative, the lowermost edge of the top view member may be provided with an inclined orientation inside the pouch. This may be advantageous as water can run off and not be trapped in the pocket formed by the top view member.

In order to hold the top view member in a closed position it is found advantageous that releasable attachment means are provided on the exterior surfaces of the sheet layers facing each other of the top member. Accordingly, in an embodiment, the releasable attachment means may comprise a hook strip and a loop strip on each of the sheets, respectively, to establish what is commonly known as a Velcro® closure.

Preferably, the first wall and the second wall are opaque films, such as beige coloured films. This gives the pouch a discrete appearance when worn by the user. However, it is realised that alternatively only one of the films may be opaque and the other transparent.

In order to improve the comfort for the user, a non-woven layer is preferably provided at the proximal side of the first wall, and preferably also at the distal side of the second wall.

It is realised that the pouch may be a drainable pouch with a closable drainage opening in the lower portion of the pouch. Alternatively, the pouch may be a disposable pouch for single use.

In the following ostomy pouches in accordance with the disclosure are described in more detail with reference to the accompanying drawings, in which:

FIG. 1 is a front view of an ostomy pouch from its distal side according to a first embodiment of the disclosure;

FIG. 2 is a front view of an ostomy pouch from its distal side according to a second embodiment of the disclosure;

FIG. 3 is a schematic cross-sectional side view of an ostomy pouch according to an embodiment of the disclosure;

Figure 6:
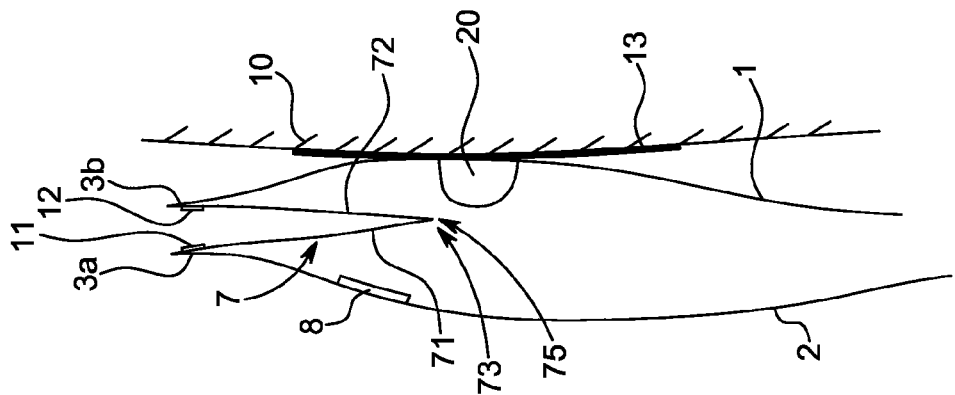
FIG. 6 is a cross-sectional side view of an open ostomy pouch according to another embodiment of the disclosure.

With reference to FIGS. 1-3, an ostomy pouch according to the preferred embodiments comprises a first, proximal side wall 1 and a second, distal side wall 2. The first and second side walls 1, 2 are joined to each other along their periphery by the peripheral seal 3. The pouch has an upper portion 4 and a lower portion 5. In the upper portion 4 of the first side wall 1 a stoma opening 6 is provided. On the distal, second side wall 2 a flatus gas filter 8 may be provided in the upper portion 4 of the pouch. In the examples shown in the figures, the lower portion 5 is provided with a closable drainage portion for draining the pouch for its content. However, by the disclosure it is realised that a closed pouch without a closable drainage opening may also be provided. On the proximal side of the pouch a comfort layer of non-woven film is provided and welded to the first side wall 1 by peripheral seals 3c and 3d. Although not shown in the figures, a non-woven layer may also be provided on the distal side of the pouch, i.e. peripherally sealed onto the second side wall 2.

The first and second side walls 1, 2 are preferably made of an opaque or at least semi-opaque film, such as a beige coloured, flexible plastic film. At the top of the upper portion 4 a top view member 7 is inserted between the first and second side walls 1, 2. This top view member 7 may comprise two layers of transparent film 71, 72 that are jointed together at their lowermost edge 73 either by heat sealing 74 (see FIGS. 3, 4 and 5) or by folding 75 (see FIG. 6) a transparent film into two opposing sheet layers 71, 72. The lowermost edge 73 may be horizontal, i.e. substantially perpendicular, to the longitudinal directions of the pouch as shown with the dotted line in FIG. 2 or the lowermost edge 73 of the top view member 7 may be inclined as shown in FIG. 1. The top view member 7 may be welded to the top of the pouch side walls 1, 2 at the sealings 3a, 3b along the top portion of the periphery of the pouch. Hereby a pocket is formed which can be opened for viewing the inside of the pouch when required.

On the opposing sides of the two sheet layers 71, 72, releasable closure members 11, 12 may be provided, such as a hook element strip 11 on one of the transparent sheet layers 71 and a loop element strip 12 on the other sheet layer 72, such as shown in the FIGS. 1-6.

Figure 5:
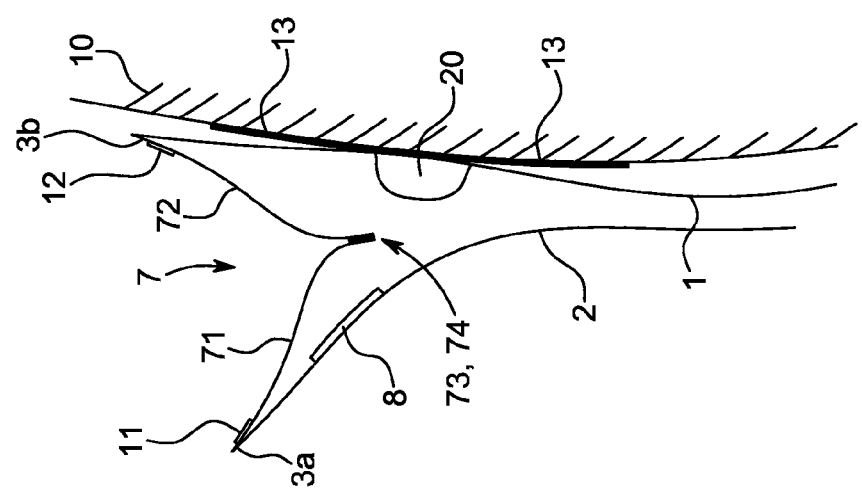
FIG. 5 is a cross-sectional side view of an open ostomy pouch according to an embodiment of the disclosure.
Figure 4:
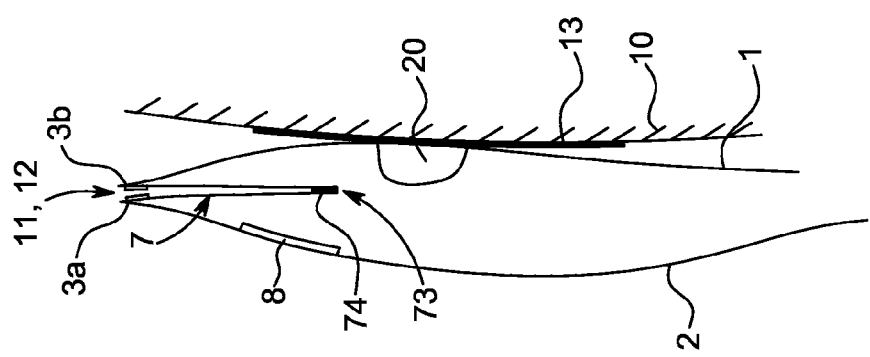
FIG. 4 is a cross-sectional side view of a closed ostomy pouch according to an embodiment of the disclosure.

In the FIGS. 4 to 6, a pouch is shown attached to the skin 10 of a wearer around the stoma 20 via an adhesive wafer 13 fitted around the opening 6 (see FIG. 3). In FIG. 4, the pouch is shown with the top view option closed, i.e. where the transparent top view member 7 is folded with its two sheet layers 71, 72 adjacent each other and with the closure members 11, 12 engaging each other. In FIG. 5, the top view member 7 is opened and the two sheet layers 71, 72 are folded apart allowing the wearer visual access to the stoma. The top view member 7 is in the embodiment shown in FIGS. 4 and 5 made by two transparent sheet members 71, 72 that are welded together at the seal 74 along the lowermost edge 73. An alternative top view member 7 is shown in FIG. 6 where the top view member 7 is made of a folded transparent sheet thereby forming the two sheet layers 71, 72 and a fold is provided along the lowermost edge 73 of the top view member 7.

In the above description and in the following, when using directional terms, such as upper portion, lower portion, horizontal orientation, and the like, these terms should be understood as relative terms as the pouch may be positioned in different orientations during use.

The invention claimed is:

1. An ostomy pouch comprising
a first pouch wall and a second pouch wall joined together along a peripheral seal to form a cavity for accommodating waste material; and said pouch having an upper and a lower portion;
an inlet provided in the first pouch wall for receiving waste into the pouch; said inlet opening being provided in the upper portion;
characterized in that
the pouch further comprises a top view member comprising at least one sheet of film forming a pocket-like structure at an upper periphery of the pouch that extends into the cavity and configured for viewing inside of the pouch, wherein at least a portion of the top view member is formed from a transparent flexible film, and wherein upper peripheries of the top view member are sealed to either the first or the second wall by peripheral seals and the rest of the top view member is closed to form the pocket-like structure having an only opening defined between the upper peripheries that are sealed to the first and the second pouch walls.

2. An ostomy pouch according to claim 1, wherein the top view member comprises first and second sheet layers which are sealed together along their lower edges to provide the lowermost edge of the top view member, and wherein the first sheet layer is sealed to the first side wall along their common peripheral edge, and wherein the second sheet layer is sealed to the second side wall along their common peripheral edge.

3. An ostomy pouch according to claim 1, wherein the top view member comprises a single sheet which is folded to form the lowermost edge and two sheet layers which are sealed to the first side wall and the second side wall, respectively.

4. An ostomy pouch according to claim 1, wherein the lowermost edge is provided in a horizontal orientation inside the pouch.

5. An ostomy pouch according to claim 1, wherein the lowermost edge is provided with an inclined orientation inside the pouch.

6. An ostomy pouch according to claim 1, wherein releasable attachment means are provided on exterior surfaces of the top member.

7. An ostomy pouch according to claim 6, wherein the releasable attachment means comprises a hook strip and a loop strip, respectively, on each of the sheets.

8. An ostomy pouch according to claim 1, wherein the first wall and/or the second wall are opaque film(s), such as beige coloured films.

9. An ostomy pouch according to claim 1, wherein a non-woven layer is provided at the proximal side of the first wall, and preferably also at the distal side of the second wall.

10. An ostomy pouch according to claim 1, wherein the pouch is a drainable pouch with a closable drainage opening in the lower portion of the pouch.

* * * * *